US009588201B1

United States Patent
Harris et al.

(10) Patent No.: US 9,588,201 B1
(45) Date of Patent: Mar. 7, 2017

(54) DETECTION USING MICROWAVE ASSISTED NQR

(71) Applicant: BAE Systems Information And Electronic Systems Integration Inc., Nashua, NH (US)

(72) Inventors: Don A. Harris, Columbia, MD (US); Michael J. Bowers, II, Sykesville, MD (US); Roland A. Gilbert, Milford, NH (US); Tadd C. Kippeny, Mount Airy, MD (US)

(73) Assignee: BAE Systems Information and Electronic Systems Integration Inc., Nashua, NH (US)

( * ) Notice: Subject to any disclaimer, the term of this patent is extended or adjusted under 35 U.S.C. 154(b) by 540 days.

(21) Appl. No.: 14/154,293

(22) Filed: Jan. 14, 2014

Related U.S. Application Data

(60) Provisional application No. 61/848,933, filed on Jan. 14, 2013.

(51) Int. Cl.
*G01V 3/00* (2006.01)
*G01R 33/44* (2006.01)
*G01R 33/36* (2006.01)

(52) U.S. Cl.
CPC ....... *G01R 33/441* (2013.01); *G01R 33/3607* (2013.01)

(58) Field of Classification Search
CPC ............ G01R 33/5608; G01R 33/4828; G01R 33/543; G01R 33/50; A61B 5/055
See application file for complete search history.

(56) References Cited

U.S. PATENT DOCUMENTS

| | | | |
|---|---|---|---|
| 6,194,898 B1 * | 2/2001 | Magnuson | G01R 33/441 324/300 |
| 6,343,534 B1 * | 2/2002 | Khanna | F41H 11/16 102/402 |

(Continued)

FOREIGN PATENT DOCUMENTS

| | | |
|---|---|---|
| EP | 0813685 | 12/2004 |
| WO | 2011126594 | 1/2011 |
| WO | 2011152887 | 1/2011 |

*Primary Examiner* — Walter L Lindsay, Jr.
*Assistant Examiner* — Frederick Wenderoth
(74) *Attorney, Agent, or Firm* — Sand & Sebolt, LPA; Daniel J. Long

(57) ABSTRACT

A system and method for detecting at least one compound in a material under test (MUT) is presented. The system includes a Nuclear Quadrupole Resonance (NQR) frequency generator that generates an NQR frequency ($f_{NQR}$) and propagates the $f_{NQR}$ frequency toward the MUT. A microwave frequency generator generates a microwave frequency ($f_{mw}$) and propagates the $f_{mw}$ frequency toward the MUT. A RF output probe detects radio frequency (RF) emissions returned from the MUT. A detector detects the at least one compound based, at least in part, on whether the RF emissions returned from the MUT include any frequencies corresponding to $f_{mw}+/-(n \times f_{NQR})$, where n is an integer of 2 or greater. In the preferred embodiment, n=2.

18 Claims, 5 Drawing Sheets

(56) References Cited

U.S. PATENT DOCUMENTS

| | | | |
|---|---|---|---|
| 6,690,168 B1 * | 2/2004 | Herron | G01R 33/02 324/318 |
| 7,411,392 B2 | 8/2008 | Fullerton | |
| 2009/0039884 A1 * | 2/2009 | Schiano | G01R 33/441 324/307 |
| 2010/0213365 A1 * | 8/2010 | Crowley | G01N 24/084 250/282 |
| 2012/0161762 A1 * | 6/2012 | Zank | G01R 33/12 324/309 |
| 2012/0161771 A1 | 6/2012 | Apostolos et al. | |

* cited by examiner

DETECTION USING MICROWAVE ASSISTED NQR

CROSS REFERENCE TO RELATED APPLICATION

This application claims priority from U.S. Provisional Application Ser. No. 61/848,933, filed Jan. 14, 2013; the disclosure of which is incorporated herein by reference.

BACKGROUND OF THE INVENTION

Field of Invention

The present invention relates generally to the detection of a target material contained within a sample material. More particularly, the present invention relates the detection of explosives and other materials. Specifically, the present invention utilizes Nuclear Quadrupole Resonance (NQR) and microwave frequencies to locate a target material so it may be evaluated and determined whether it is an explosive or another material.

BACKGROUND INFORMATION

Since the earliest days of explosive and contraband detection, people have been trying to gain advantages over their opponents. These advantages have become more desirable ever since the advent of extremely deadly explosives, and highly illegal contraband. One desirable advantage is the ability to remotely detect an explosive within a set of sample material. This sample material could be in the ground, so as to detect an explosive mine or the sample material may be separated from the ground, so as to detect an explosive bomb or contraband contained in a box.

Atoms and molecules often have resonance frequencies. If one emits a photon at one of these resonance frequencies, the material will absorb this photon and store it for some amount of time before later discharging this energy. It is has been found that in nature the molecules which absorb such energy later fall to a lower energy state.

One of the ways for the material to emit energy is through spontaneous emission where a photon of exactly the same energy that is impinging on the material is thrown off in a random direction at random times.

The second way of getting rid of the energy absorbed by the material is through process of stimulated emission in which a photon at the appropriate energy gets near the molecule it stimulates the molecule. Later, when the molecule drops to the lower energy state it emits a photon that is in phase with the original photon.

The energy that is thrown off either in spontaneous emission or stimulated emission results in a narrow spectral line. In fact, the line is generally considered to be a single line that exists at a given wavelength or frequency.

Nuclear quadrupole resonance (NQR) is a branch of radio-frequency spectroscopy (which includes the study of spectral lines). NQR has been utilized in the past to detect the presence of specific molecules, including explosives. Explosives generally involve the use of nitrogen or nitrogen bonded with other elements. When NQR was utilized in the past, it was used to detect the presence of molecules due to the molecular elements that are bonded together such that the molecules absorb energy at, for instance, as many as eight different energy levels or spectral lines. It turns out that at least three of the energy levels tend to be prominent. Although in some materials, there are upwards of all eight energy levels for one bond. If one has many bonds, there may be many dozens of spectral lines. In order to detect the presence of a molecule one usually is looking to pump energy right at the top of one of the spectral lines and look for energy coming back at the same frequency.

A further background explanation of NQR was originally published in U.S. Pat. No. 6,194,898 ('898 Patent). The '898 Patent explains that NQR exploits the inherent electrical properties of atomic nuclei. Nuclei with non-spherical electric charge distributions possess electric quadrupole moments. Quadrupole resonance arises from the interaction of the nuclear quadrupole moment of the nucleus with the local applied electrical field gradients produced by the surrounding atomic environment. NQR does not require an external static magnetic field.

Any chemical element's nucleus having a spin quantum number greater than one half can exhibit quadrupolar resonance. Many substances (approximately 10,000) have been identified that exhibit quadrupolar resonance, among such nuclei being: $^7$Li, $^9$Be, $^{14}$N, $^{17}$O, $^{23}$Na, $^{27}$Al, $^{35}$Cl, $^{37}$Cl, $^{39}$K, $^{55}$Mn, $^{75}$As, $^{79}$Br, $^{81}$Br, $^{127}$I, $^{197}$Au, and $^{209}$Bi. It so happens that some of these quadrupolar nuclei are present in explosive and narcotic (i.e., contraband) materials, among them being nitrogen ($^{14}$N), chlorine ($^{35}$Cl, $^{37}$Cl), oxygen ($^{17}$O), sodium ($^{23}$Na), and potassium ($^{39}$K). The most studied quadruple nucleus for explosives and contraband detection is nitrogen.

In solid materials, electrons and atomic nuclei produce electric field gradients. These gradients modify the energy levels of any quadrupolar nuclei and hence their characteristic transition frequencies. Measurements of these frequencies or relaxation time constants, or both, can indicate not only which nuclei are present but also their chemical environment.

When an atomic quadrupolar nucleus is within an electric field gradient, variations in the local field associated with the field gradient affect different parts of the nucleus in different ways. The combined forces of these fields cause the quadrupole to experience a torque, which causes it to precess about the electric field gradient. Precessional motion generates an oscillating nuclear magnetic moment. An externally applied radio frequency (RF) magnetic field in phase with the quadrupole's precessional frequency can tip the orientation of the nucleus momentarily. The energy levels are briefly not in equilibrium, then the energy levels immediately begin to return to equilibrium. As the nuclei return to equilibrium, they produce an RF signal, known as the free induction decay (FID) or return frequency. A pick-up coil detects the signal, which is subsequently amplified by a sensitive receiver to measure its characteristics.

One distinguishing feature of an NQR response is the NQR relaxation times. Relaxation times are a measure of the nuclei's rate of return to the equilibrium state following disturbance by an RF irradiation pulse. Relaxation times are compound-, temperature-, and pressure-specific. Relaxation times also determine the repetition rate and timing of RF pulses required for exciting and detecting a specific NQR signal. Relaxation times from pulsed systems can be as long as eight seconds for some materials like TNT.

The '898 Patent discloses a method for detecting a target substance within a class of explosives and narcotics containing quadrupolar nuclei in a specimen. The method employs the phenomenon of nuclear quadrupole resonance (NQR) in a pulsed detection system and includes the steps of: forming a scanner having an RE Coil for a probe; entering known characteristics of NQR signals of target substances in memory in a signal processor in the detection system; providing programmed timing pulses to the detection system; inserting the specimen within the volume enclosed by the RF coil; then automatically adaptively tuning the RE coil to maximize power transfer efficiency for RF signals transmitted within the RF coil cavity; providing excitation RF pulses of a predetermined frequency to the RF coil; transmitting the RE pulses into the cavity formed by the RF coil and creating a flux field with the RF coil to which the specimen is subjected; detecting by the RF coil the NQR signals emitted by target substances within the specimen; processing the NQR signals and comparing them to known signal characteristics to determine whether the detected NQR signals indicate the presence of a target substance; and indicating whether the target substance is present in the specimen.

Problems and issues may still arise with the '898 Patent, namely, with respect to the detection of explosives or other contraband. One problem is that certain non-explosive materials also contain nitrogen bonds having energy levels substantially equal or in a similar frequency range as an explosive or contraband material. An additional problem results from the RF pulses. The RF pulses require a large amount of power. The amount of power needed to operate the system of the '898 patent is 1 to 2 KW RF power amplifier for examining airline baggage for explosives. This system would be unsafe for direct human use.

Further, an issue arises where the RF pulses would require a relaxation time (the time between the broadcasted pulse signals and a receiver being able to locate a return frequency signal) in the range of about 3 to 8 seconds for detecting trinitrotoluene (TNT). This relaxation time is too long for any real world application requiring scanning of moving people. This is because the device would have to stop irradiating signals and "listen" for the NOR emission or return frequency until sample material would stop resonating prior to device sending out another pulse. Or, this problem would also arise when the pulsed system would be transmitting signals while simultaneously trying to measure or listen for the return frequency.

Another issue with pulsed NOR detection systems is there is a large dynamic range in decibels (db, the ratio between two values of a physical quantity, power and intensity [amplitude]). The dynamic range can be as large as 150 db to measure a return frequency for a target material within a sample material. For example, to locate a nitrate in a sample material, an electromagnetic pulsed signal is transmitted/broadcasted at 0 db (1 to 1 ratio) into the sample material. The expected NQR emitted signal from any nitrate would be in an expected range from about −125 db to about −150 db. This is an extremely low level of return signal strength, making it difficult to positively identify the nitrate. Therefore, what is needed is a better way for detecting explosives and other contraband.

SUMMARY

The preferred embodiment of the invention includes a system for detecting at least one compound in a material under test (MUT). The system includes a Nuclear Quadrupole Resonance (NQR) frequency generator that generates an NQR frequency ($f_{NQR}$) and propagates the $f_{NQR}$ frequency toward the MUT. A microwave frequency generator generates a microwave frequency ($f_{mw}$) and propagates the $f_{mw}$ frequency toward the MUT. A RE output probe detects radio frequency (RF) emissions returned from the MUT. A detector detects the at least one compound based, at least in part, on whether the RF emissions returned from the MUT include any frequencies corresponding to $f_{mw}+/-(n \times f_{NQR})$, where n is an integer of 2 or greater. In the preferred embodiment, n=2.

Another configuration of the preferred embodiment is a method of determining if a compound is present in a MUT. The method begins by propagating a nuclear quadrupole resonance (NQR) frequency ($f_{nqr}$) toward a material. A frequency that is at least double the NQR frequency, $f_{dbl}$, is also propagated toward the material. A determination is then made to determine if the returned signal has a frequency of $f_{dbl}+/-(n \times f_{dbl})$ wherein n is an integer=2 or greater. A returned frequency of $f_{dbl}+/-(n \times f_{nqr})$ indicates the compound is present in the MUT. If the compound (nitrogen for example) is present the method can generate an indication the compound is present. The indication or alarm can be a visual indicator and/or an audio indicator.

BRIEF DESCRIPTION OF SEVERAL VIEWS OF THE DRAWINGS

One or more preferred embodiments that illustrate the best mode(s) are set forth in the drawings and in the following description. The appended claims particularly and distinctly point out and set forth the invention.

The accompanying drawings, which are incorporated in and constitute a part of the specification, illustrate various example methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

Similar numbers refer to similar parts throughout the drawings.

DETAILED DESCRIPTION

A new phenomenon has recently been discovered which determines the NQR frequency by measuring the effects on the microwave scattering properties of a nitrogen compound when it is excited at any of its NQR frequencies. At an NQR frequency, the quadrupoles align themselves within the compound to produce small changes in the polarization of the material. These small changes in polarization can be interpreted as small changes in the dielectric constants of the compound that oscillates at the NQR frequency. The preferred embodiment makes use of that property to illuminate a compound (nitrogen for example) in a material under test (MUT) with a much higher frequency signal, such as with a microwave signal, and then measure the scattered signal from that compound. The reflection (called scattering) properties are modulated accordingly; appearing as amplitude modulation sidebands. The offset of these sidebands from the microwave carrier frequency is at twice the NQR frequency. The likely reason for the doubling in modulation frequency is that the dielectric constant changes twice during a period of HF signal excitation at the NOR frequency. Therefore this measurement approach does not measure the NOR emissions as previous systems do, but measures the effects of NOR resonance on the scattering properties of a test compound in a MUT at quieter frequencies.

The Antennas used in the preferred embodiment are much smaller than high frequency (HF) antennas at microwave frequencies. The preferred embodiment of a microwave assisted NQR system has the ability to measure the NQR frequency of a compound at low power in free space conditions indoors and outdoors at some standoff distance in air as well as making measurement on materials buried in dirt, mud, water and in other environments. The preferred embodiment can be used in systems employed in land mine and mine sweeping equipment as well as looking for explosives in baggage at airports and warehouses. Since many drugs also contain nitrogen substances, this system can also be modified to look for drugs in containers or on persons walking through a portal in airports.

Figure 1:
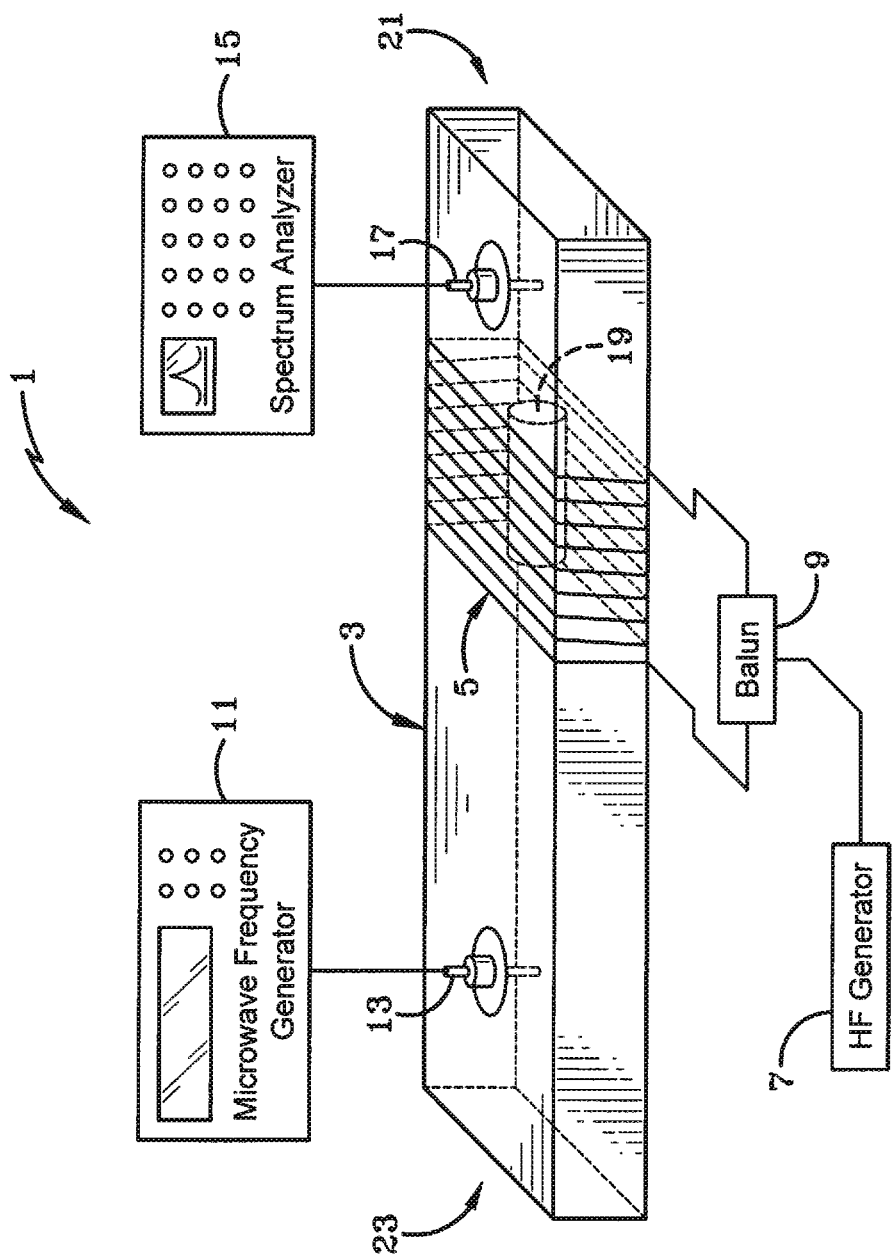
FIG. 1 illustrates an example of the preferred embodiment of a microwave assisted NQR system for detecting a compound.

FIG. 1 illustrates the preferred embodiment of a microwave assisted NQR system 1 (MANS). The system 1 includes a waveguide 3 that has an open first end 21 and an open second end 23. For example, the waveguide 3 could be formed in a hallway with people passing through the open ends 21, 23 or it could be formed in a baggage inspections unit with luggage or other handheld items passing through the waveguide 3. A high frequency (HF) coil 5 is formed around a center area of the waveguide 3 and is connected to an HF generator 7 through a balun. A microwave frequency generator 11 is configured to inject microwave radio frequency (RF) signals into the waveguide 3 through an RF input probe 13. An RF output probe 17 collects output RF signals returned from a material under test (MUT) 19 and sends them to a spectrum analyzer 15. This figure illustrates an example MUT 19 passing through the HF coil 5.

Figure 2:
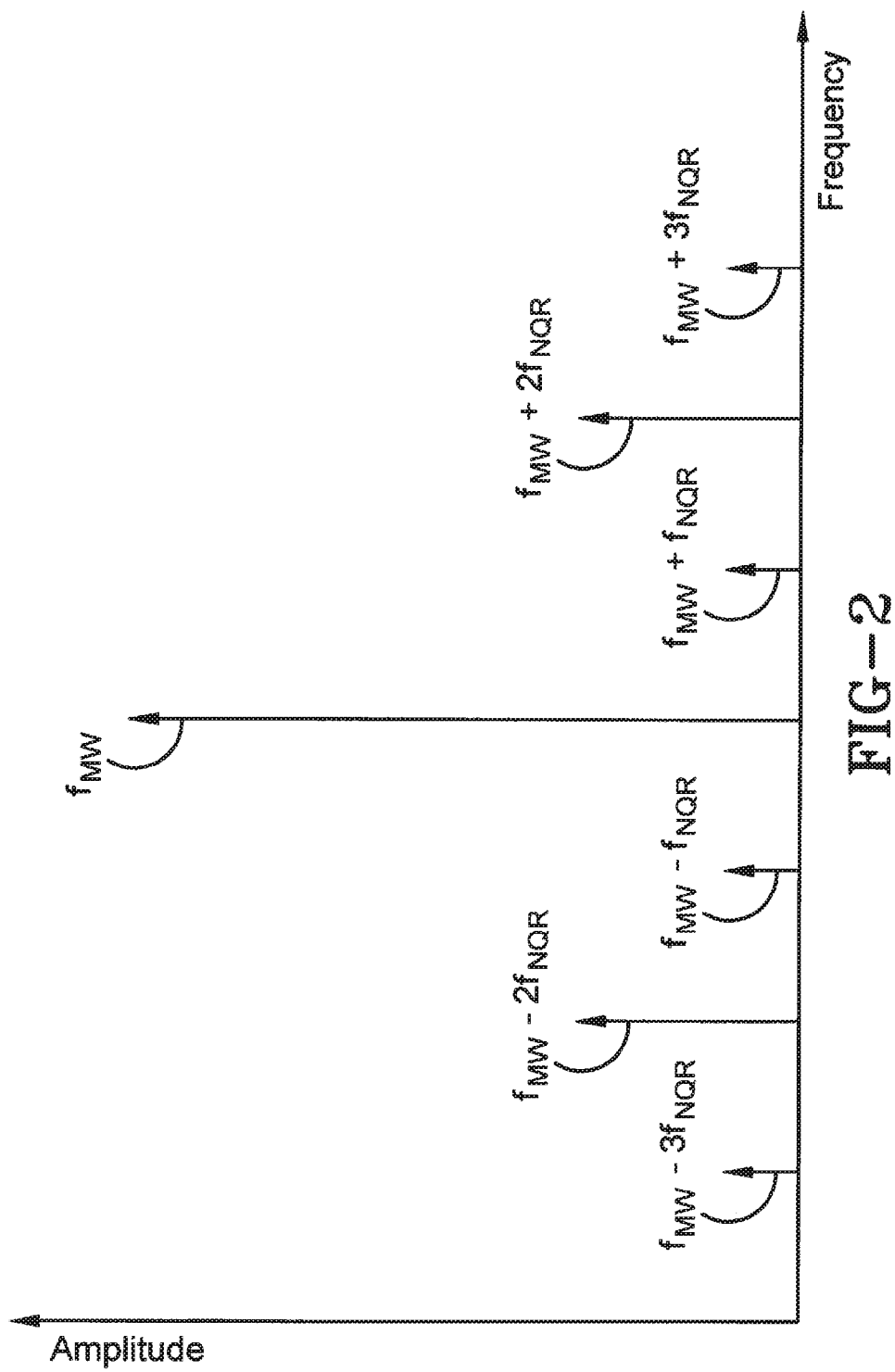
FIG. 2 illustrates an example spectra returned from a compound energized by the preferred embodiment of a microwave assisted NQR system.

Having described the preferred embodiment of a microwave assisted NQR system 1, its use and operation will now be described. As is traditionally done, the HF generator is used to generate an HF nuclear quadrupole resonance (NQR) frequency $f_{NQR}$ that is used to excite a particular material. In addition to the $f_{NQR}$ a microwave frequency $f_{mw}$ is also generated by the microwave frequency generator 11 and injected into the waveguide by the RF input probe 13. The primary novelty of this embodiment is that the spectrum analyzer 15 looks for an output frequency received from the RF output probe that is $f_{mw}+/-(2 \times f_{NQR})$ that is returned by an excited compound (such as nitrogen or another compound) in the MUT 19. It has been observed that this signal is much larger in magnitude and can much more easily be detected than looking for a response at $f_{NQR}$ alone or at $f_{mw}+/-f_{NQR}$ alone. The return signal of $f_{mw}+/-(2 \times f_{NQR})$ is also non-intermittent while the $f_{mw}+/-f_{NQR}$ frequencies are often intermittent and non-measurable. Additionally, the $f_{mw}+/-(2 \times f_{NQR})$ return signal frequencies have much more power than other returned signals from the material under test 19 so that it is more easily detected. FIG. 2 illustrates in a graphical way these results that are completely unexpected to one of ordinary skill in the art. This means that explosives and other materials can be more accurately detected with fewer false positives than looking for a $f_{mw}+/-f_{NQR}$ return signal or another signal or response. Additionally, lower power RF signals can be injected into the test material 19 and/or smaller antenna could be used to detect the returned RF signal.

U.S. Pat. No. 7,411,392 issued to Fullerton (Fullerton) discloses an NQR system that injects two frequencies, a first frequency (NQR frequency) and a second frequency, into a material under test (MUT) and using the second frequency to observe changes in a property of the MUT caused by the first frequency. For example, see column 2, lines 64-66 of Fullerton. Alternatively, Fullerton discloses in column 4, lines 35-51 modulating the NOR signal and then later looking for that modulation on the second signal.

Figure 3:
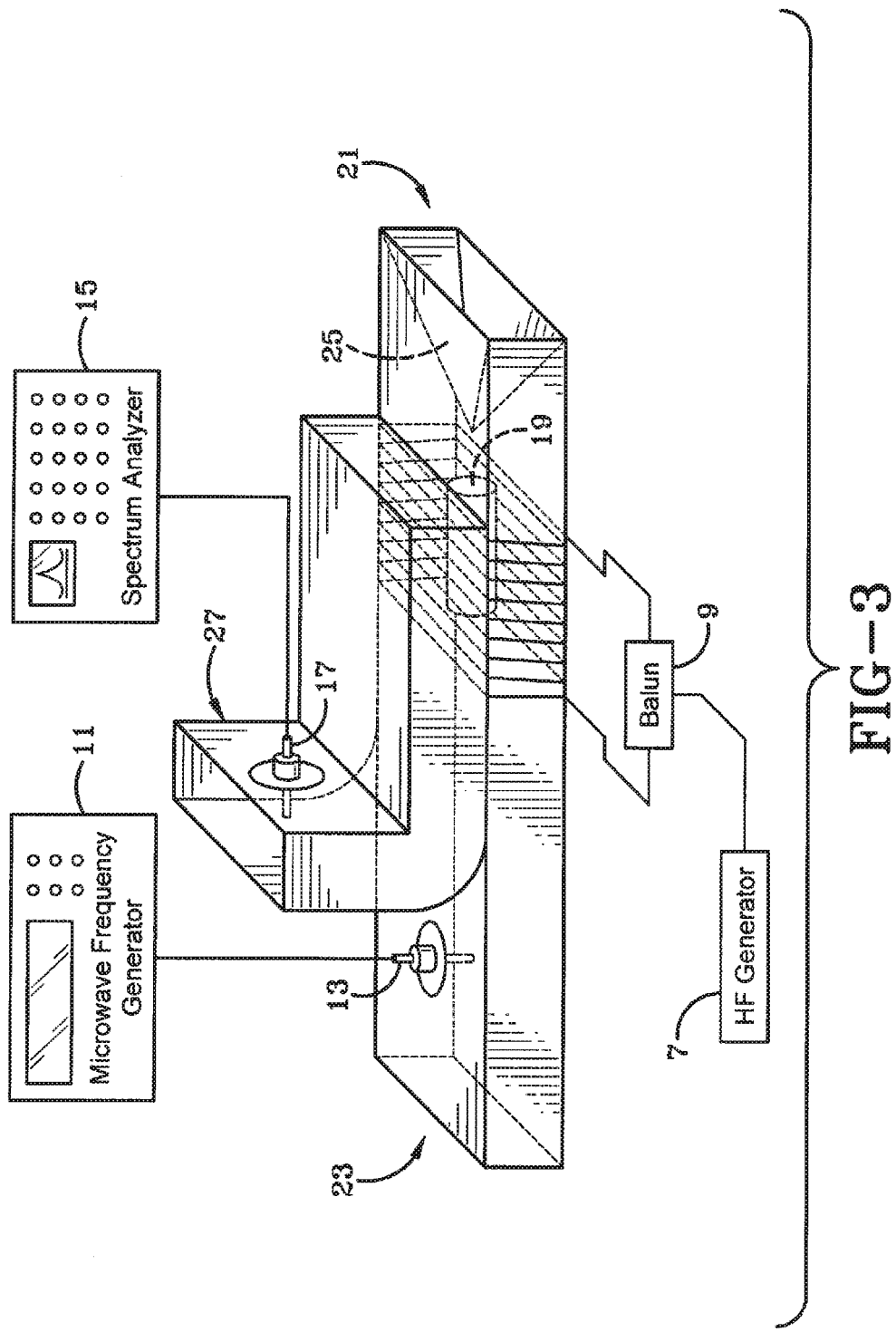
FIG. 3 illustrates another example configuration of the preferred embodiment of a microwave assisted NQR system for detecting a compound.

In column 5, lines 4-6 Fullerton discloses using a second signal that is unmodulated. However, Fullerton states that the reflected unmodulated second signal is "analyzed only for the modulation effect of the actual RF frequency of the first signal" (emphasis added). This actually teaches away from looking for a $f_{mw}+/-(2 \times f_{NQR})$ return signal as detected by the preferred embodiment. Dependent claim 3 of Fullerton similarly only claims observing "for the presence of modulation at the frequency of the first signal". Thus, Fullerton illustrates that looking for a return frequency $f_{mw}+/-(n \times f_{NQR})$ when n=2 or greater was an unexpected result to one of skill in the art. FIG. 3 illustrates another configuration of the preferred embodiment that has its RF output probe 17 connected to a reflection chamber 27. Here, the right side 21 of the waveguide 3 has a waveguide termination 25 so that the signal emitted from the sample or material under test 19 is reflected up to the reflection chamber 27 and toward the RF output probe 17. The other components in FIG. 3 are the same as FIG. 1 and operate in a similar way.

Figure 4A:
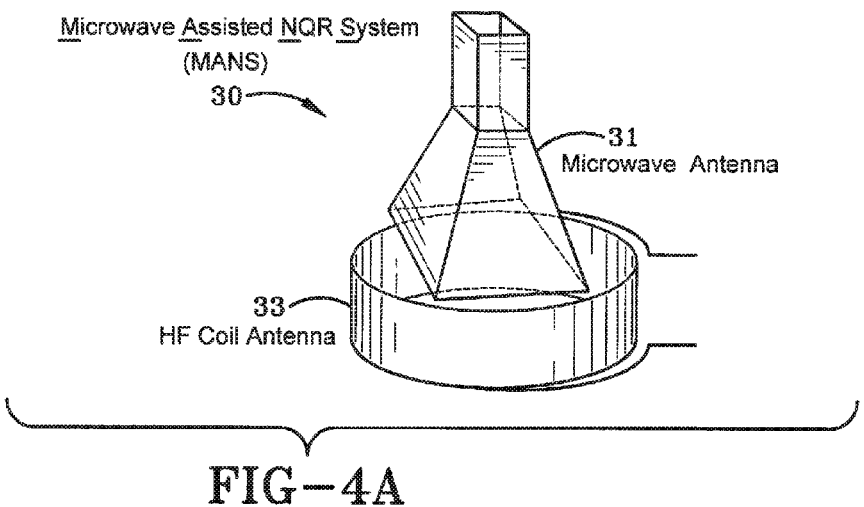
FIGS. 4A and 4B illustrate another example configuration of the preferred embodiment of a microwave assisted NQR system for detecting a compound that uses a horn antenna adjacent a coil of wire.
Figure 4B:
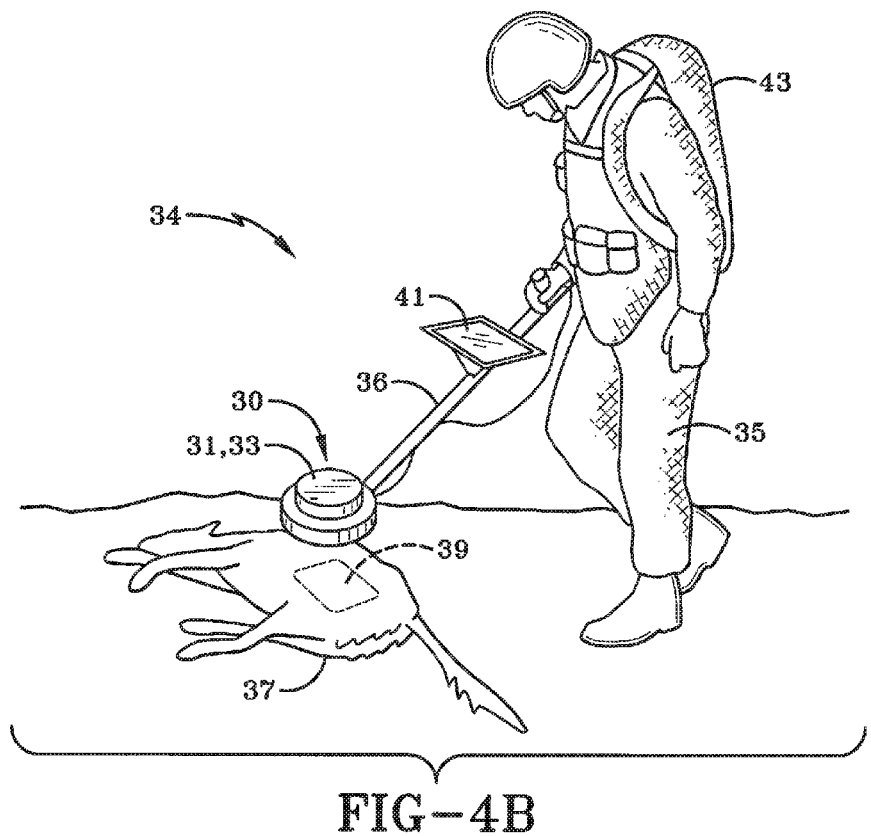

FIGS. 4A-B illustrated another configuration of a MANS system 30. This system 30 includes an HF coil antenna 33 that operates similar to the HF coil 5 of FIGS. 1 and 3. It also includes a microwave antenna 31 that operates similar to the right side of the waveguide 3 of FIG. 1 to guide a returned RF signal to an RF output probe 17. Of course this MANS system 30 would have HF and microwave frequency generators, a spectrum analyzer and other components as needed but these are not all shown for clarity. Those of ordinary skill in the art will appreciate that other components could be used and that it may be possible to user other frequencies than HF and microwave frequencies. For example, a different analyzer than a spectrum analyzer may be used to determine if a returned frequency corresponding to the material under test (MUT) is present.

FIG. 4B illustrates the MANS system 30 of FIG. 4A implemented in an example explosives detection system 34. The explosive detection system 34 includes the MANS system 30 with its HF coil 33 and microwave antenna 31 with the MANS system 30 attached near one end of an elongated pole 36 similar to a traditional metal detector. The system 34 includes a display 41 and an electronic module 43.

In operation, a soldier 35 holds one end of the pole 36 and scans with the MANS system 30 at the other end of the pole 36 over a surface that he desires to check for explosives. This figure illustrates the soldier 35 scanning a dead animal 37 that he suspects has had explosives 39 hidden inside. An HF generator and a microwave frequency generator inside the electronic module 43 generate the appropriate signals to respectively be transmitted from the HF coil antenna 33 and the microwave antenna 31. These generators can operate similar to the HF coil antennas and the microwave antennas discussed above.

Signals received back from the explosives 39 are analyzed by a spectrum analyzer (or other logic) in the electronics module to determine if frequency(s) associated with explosive(s) are present or not. When these frequencies are present, it is an indication that the explosives 39 are within range of the MANS system 30. When the system 34 detects the explosives have been detected, the electronic module can generate an appropriate message and/or image to be displayed on the display 41. An Audio warning can also be generated upon detection of the explosives 39.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 5:
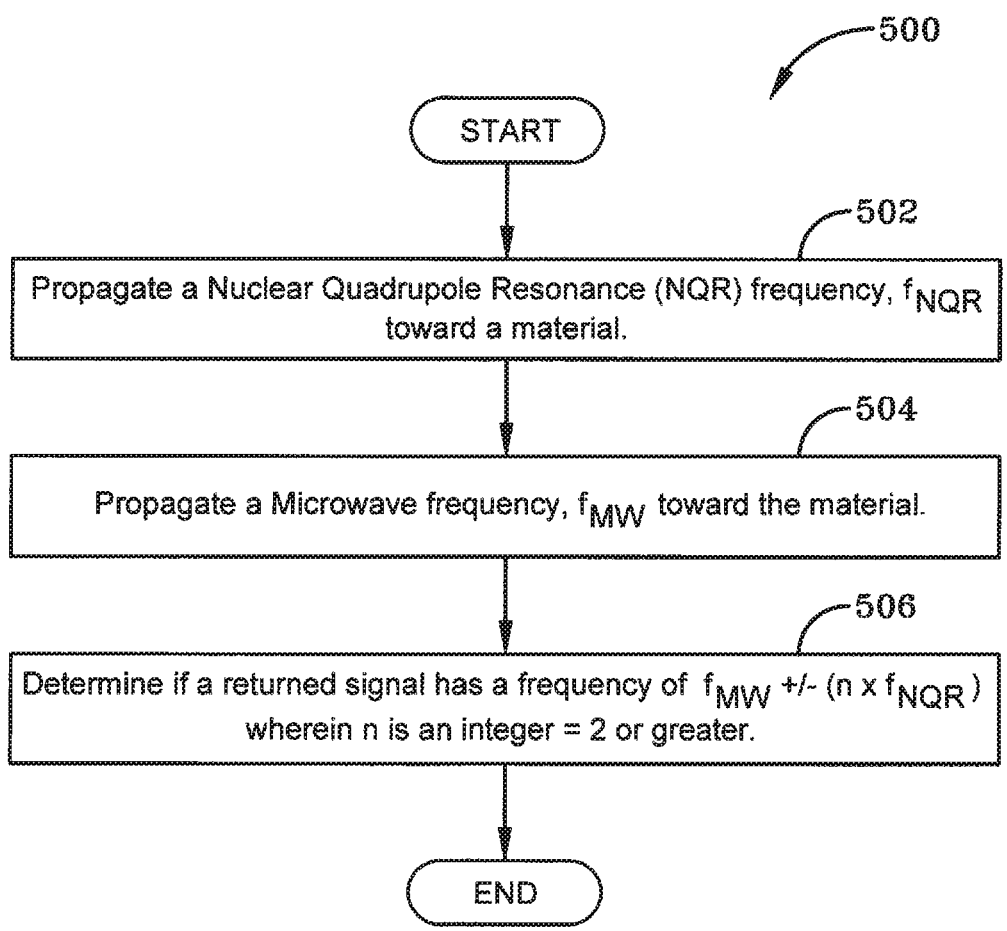
FIG. 5 illustrates an example configuration of the preferred embodiment that is a method of using microwaves and NQR frequencies to detecting a compound.

FIG. 5 illustrates a method 500 of determining if a compound is present in a MUT. The method 500 begins by propagating, at 502, a nuclear quadrupole resonance (NQR) frequency ($f_{NQR}$) toward a material. A frequency that is at least double the NQR frequency, $f_{dbl}$, is propagated toward the MUT, at 504. The $f_{nqr}$ frequency and the $f_{dbl}$ frequency can be propagated similar to how the $f_{NQR}$ and $f_{mw}$ frequencies, respectively, generated and propagated as discussed above. A determination is made, at 506, to determine of the returned signal has a frequency of $f_{dbl}+/-(n \times f_{dbl})$ where n is an integer=2 or greater. A returned frequency of $f_{dbl}+/-(n \times f_{nqr})$ indicates the compound is present in the MUT. If the compound (nitrogen for example) is present, the method can generate an indication that the compound is present. The indication could be an alarm and can be a visual indicator and/or an audio indicator.

In the foregoing description, certain terms have been used for brevity, clearness, and understanding. No unnecessary limitations are to be implied therefrom beyond the requirement of the prior art because such terms are used for descriptive purposes and are intended to be broadly construed. Therefore, the invention is not limited to the specific details, the representative embodiments, and illustrative examples shown and described. Thus, this application is intended to embrace alterations, modifications, and variations that fall within the scope of the appended claims.

Moreover, the description and illustration of the invention is an example and the invention is not limited to the exact details shown or described. References to "the preferred embodiment", "an embodiment", "one example", "an example", and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in the preferred embodiment" does not necessarily refer to the same embodiment, though it may.

What is claimed is:

1. A system for detecting at least one compound in a material under test comprising:

a Nuclear Quadrupole Resonance frequency generator configured to generate an Nuclear Quadrupole Resonance frequency ($f_{NQR}$) and adapted to propagate the Nuclear Quadrupole Resonance frequency to the material under test;

a microwave frequency generator to generate a microwave frequency ($f_{MW}$) and adapted to propagate the microwave frequency to the material under test;

a radio frequency input probe for to propagate the Nuclear Quadrupole Resonance frequency to the material under test;

a radio frequency output probe adapted to detect returned radio frequency signals which are returned from the material under test;

a waveguide for receiving the returned radio frequency signals which are returned from the material under test;

wherein the radio frequency input probe is near a first end of the waveguide and the radio frequency output probe is near a second end of the waveguide;

wherein the material under test is located in the waveguide and located between the radio frequency input probe and the radio frequency output probe; and a detector adapted to detect the at least one compound based, at least in part, on whether the returned radio frequency signals which are returned from the material under test include frequencies corresponding to $f_{MW}+/-(n \times f_{NQR})$, where n is an integer of 2 or greater.

2. The system for detecting the at least one compound of claim 1 wherein n=2.

3. The system for detecting at least one compound of claim 1 further comprising:

a coil of wire wrapped inside the waveguide, wherein the Nuclear Quadrupole Resonance frequency generator is configured to propagate the Nuclear Quadrupole Resonance frequency to the material under test through the coil of wire.

4. The system for detecting at least one compound of claim 3 further comprising:

a balun connected between the Nuclear Quadrupole Resonance frequency generator and the coil of wire.

5. The system for detecting at least one compound of claim 3 wherein the waveguide is rectangular in shape with open opposite ends.

6. The system for detecting at least one compound of claim 3 wherein the coil is located near a center of the waveguide.

7. The system for detecting at least one compound of claim 1 wherein the waveguide is constructed to allow people to walk through within the waveguide without being aware the system is devised to detect at least one compound.

8. The system for detecting at least one compound of claim 1 wherein the detector further comprises:

a spectrum analyzer.

9. The system for detecting at least one compound of claim 8 wherein the spectrum analyzer further comprises:

a 1 kHz window filter and is configured to detect a return frequency of $f_{MW}+(2 \times f_{NQR})$ with a single scan of the 1 kHz window filter.

10. The system for detecting at least one compound of claim 1 wherein $f_{MW}$ between 3 Gigahertz (GHz) and 7 GHz.

11. The system for detecting at least one compound of claim 1 further comprising:

a horn antenna configured to receive the radio frequency emissions returned from the material under test; and a coil of wire configured to propagate the Nuclear Quadrupole Resonance frequency to the material under test.

12. The system for detecting at least one compound of claim 1 wherein the coil of wire is adjacent the horn antenna.

13. The system for detecting at least one compound of claim 1 further comprising:
   a directional coupler connecting the horn antenna, the microwave frequency generator and the detector together.

14. The system for detecting at least one compound of claim 1 further comprising:
   an elongated member;
   a handle attached to the elongated member, wherein the entire system is handheld, and wherein the horn antenna and coil are adapted to be swept back and forth like a traditional metal detector antenna.

15. The system for detecting at least one compound of claim 1 wherein the compound further comprises:
   nitrogen.

16. A method of determining at least one compound in a material under test comprising steps of:
   providing a Nuclear Quadrupole Resonance frequency generator;
   providing a radio frequency input probe for to propagate the Nuclear Quadrupole Resonance frequency to a material under test;
   providing a radio frequency output probe to detect returned radio frequency signal returned from the material under test;
   providing a waveguide for receiving the returned radio frequency signal;
   wherein the radio frequency input probe is near a first end of the waveguide and the radio frequency output probe is near a second end of the waveguide;
   propagating a Nuclear Quadrupole Resonance frequency ($f_{NQR}$) toward the material under test;
   propagating a frequency that is at least double the Nuclear Quadrupole Resonance frequency ($f_{DBL}$) toward the material under test;
   detecting the returned radio frequency signal from the material under test; and
   determining if the returned radio frequency signal has a frequency of $f_{DBL}+/-(n \times f_{NQR})$ where n is an integer=2 or greater, and wherein the returned frequency radio signal of $f_{DBL}+/-(n \times f_{NQR})$ indicates the compound is present in the material under test.

17. The method of claim 16 further comprising a step of:
   generating an indication the compound is present when there is the returned signal of $f_{MW}+/-(n \times f_{NQR})$.

18. The method of claim 17 wherein the indication further comprises:
   at least one of the group of: a visual indicator and an audio indicator.

* * * * *